United States Patent [19]
Powers et al.

[11] Patent Number: 5,475,232
[45] Date of Patent: Dec. 12, 1995

[54] METHOD FOR ELUTION OF A RADIOISOTOPE ACCORDING TO AN ELUTION RUN SCHEDULE

[75] Inventors: Wesley Powers, Bensalem, Pa.; Jimmie C. McDonald, Jackson, Miss.

[73] Assignee: Syncor International Corp., Chatsworth, Calif.

[21] Appl. No.: 231,022

[22] Filed: Apr. 21, 1994

Related U.S. Application Data

[63] Continuation of Ser. No. 994,985, Dec. 22, 1992.

[51] Int. Cl.$^6$ ................................................ A61K 43/00
[52] U.S. Cl. ................................................ 250/432 D
[58] Field of Search ............... 250/432 PD; 252/645; 423/2; 128/659; 600/3

[56] References Cited

U.S. PATENT DOCUMENTS

| | | | |
|---|---|---|---|
| 3,997,784 | 12/1976 | Picunko et al. | 250/432 PD |
| 5,039,863 | 8/1991 | Matsuno et al. | 250/432 PD |

*Primary Examiner*—Jack I. Berman
*Attorney, Agent, or Firm*—Pretty, Schroeder, Brueggemann & Clark

[57] ABSTRACT

A method that provides a preferred generator profile that includes a set of generators, described in terms of their size, calibration and day of receipt, that will meet radioisotope requirement for a location for a preselected period of time. The method also selects generators for elution of radioisotope and determines an elution schedule which allocates elution of the generators throughout the preselected period of time so that the radioisotope requirement is met while avoiding undue wastage of radioactivity.

12 Claims, 3 Drawing Sheets

METHOD FOR ELUTION OF A RADIOISOTOPE ACCORDING TO AN ELUTION RUN SCHEDULE

This is a continuation of copending application Ser. No. 07/994,985 filed on Dec. 22, 1992.

BACKGROUND OF THE INVENTION

1. Field of the Invention

This invention relates generally to methods for determining the calibration, size and number of generators to produce predetermined levels of radioisotopes and, more particularly, to methods to provide a preferred generator profile of the generators required to meet a predetermined requirement of radioisotopes.

2. Description of the Related Art

In recent years, diagnostic nuclear medicine has proven to be of enormous value to the medical community. Procedures for imaging and detecting abnormalities in the brain, liver, lungs, bones, and the like have been well developed and are routinely used. These procedures are based on the tendency of the body to concentrate some chemical form of a particular gamma ray emitting isotope in the organ of interest. Subsequent scanning of the organ with a gamma ray camera provides an image of the organ from which diagnostic information can be obtained.

It has long been known that the introduction into an organism of compounds containing (or "labeled" with) a radioisotope can provide insight into the anatomy and physiology of the organism. These compounds, generally referred to as radiopharmaceuticals, are particularly useful in diagnostic techniques which involve studying the structure or function of various internal organs, e.g., the brain, with radiation detection means. For diagnostic work, isotopes with a short half life and an emission spectrum rich in gamma rays (as opposed to beta particles) are preferred. It is clear that the radioisotope with optimum nuclear properties (half-life, gamma ray energy, and the like) for medical gamma ray scanning is $^{99m}Tc$, or "Tc-99m."

The metastable isotope Tc-99m has a 6 hour half-life and an emission spectrum of 99% gamma radiation at 140 KeV, which is well suited for techniques of diagnostic nuclear medicine. Tc-99m has a high specific activity, 5.28×109 millicuries per gram, and a convenient rapid rate of decay. For the researcher or clinician, the emission spectrum of Tc-99m can provide high levels of accuracy in radiodiagnostic measurements and calculations. In recent years, Tc-99m has become readily available in hospitals through the use of selective elution or removal of that radioisotope from a so-called molybdenum-99 (Mo-99) generator.

The isotope Mo-99 produces Tc-99m as a radioactive decay product and Tc-99m can be removed from a Mo-99 generator by eluting the generator. After an elution is made, the generator will start to regenerate Tc-99m and then can be re-eluted in a few hours when minimum levels of Tc-99m have been generated. However, the amount of Tc-99m obtained from an elution depends on several factors, including the amount of Mo-99 in the generator, the amount of time elapsed since the generator was last eluted, and variable factors in the eluting environment that influence elution efficiency.

A generator is described by several parameters, including the manufacturer of the generator and its size and calibration. The size of a generator is not the physical size, but rather the amount of Mo-99, expressed in terms of millicuries (mCi), in the generator. The calibration of a generator is the day of the week that the generator contains the labelled activity. For example, a Monday calibrated 1800 mCi generator will contain 1800 mCi on Monday and a Thursday calibrated 1800 mCi generator will contain 1800 mCi on Thursday. These two generators are labelled as the same size, 1800 mCi, and will cost the same, yet they will produce greatly different Tc-99m yields on a given day. The day of the week a generator is received is also a parameter for its identification. The earlier it is received after calibration, the more activity a generator will have.

The short half-life of Tc-99m (six hours) significantly decreases a pharmacy's ability to store it. The half-life of a Mo-99 generator is 3 days, which is a more reasonable amount of time. However, meeting weekly requirements of Tc-99m requires significant guess work and estimation as to the level of Tc-99 available in a Mo-99 generator at a given time. In the past, scheduling of deliveries of generators has been based upon experience. This often resulted in an inaccurate determination of a generator profile, that is, the specification of generators, in terms of the manufacturer, size, calibration and date of delivery, for a preselected period of time. Accordingly, there is a need for a method to provide a preferred generator profile, by size and calibration, that will meet a pharmacy's requirements of radioisotopes, while avoiding undue wastage of radioisotopes. The present invention fulfills this need.

SUMMARY OF THE INVENTION

Briefly, and in general terms, the present invention resides in a method that determines the set of generators, in terms of size, calibration and day of receipt, that will meet the radioisotope requirement of a pharmacy or other suitable location for the preselected period of time and in an efficient manner that greatly reduces, if not largely eliminates, undue wastage of radioactivity. The method also determines an elution schedule that allocates elution of generators throughout the preselected period of time.

More specifically, the present invention comprises a method for providing a preferred generator profile for elution of a radioisotope, including selecting a first set of generators; determining qualified generator profiles, wherein each qualified generator profile includes a second set of generators, selected from the first set of generators, such that the generators in each qualified generator profile are capable of producing, by time and amount, an output of radioisotope not less than an amount of radioisotope required for a preselected period of time; and determining a preferred generator profile from the list of qualified generator profiles.

In a more detailed aspect of the preferred embodiment of the present invention, the preferred profile generators are eluted in such a manner that they produce, by time and amount, an output of radioisotope not less than the amount of radioisotope required for the preselected period of time. In addition, the preferred method determines an elution schedule that will efficiently utilize the generators included in the preferred generator profile. The elution run schedule includes a third set of preferred profile generators, for each elution run, that will meet its radioisotope requirements with the least amount of available radioisotope.

Other features and advantages of the present invention should become apparent from the following description of the preferred method, taking in conjunction with the accompanying drawings, which illustrate, by way of example, the principals of the invention.

DESCRIPTION OF THE PREFERRED EMBODIMENT

Figure 1:
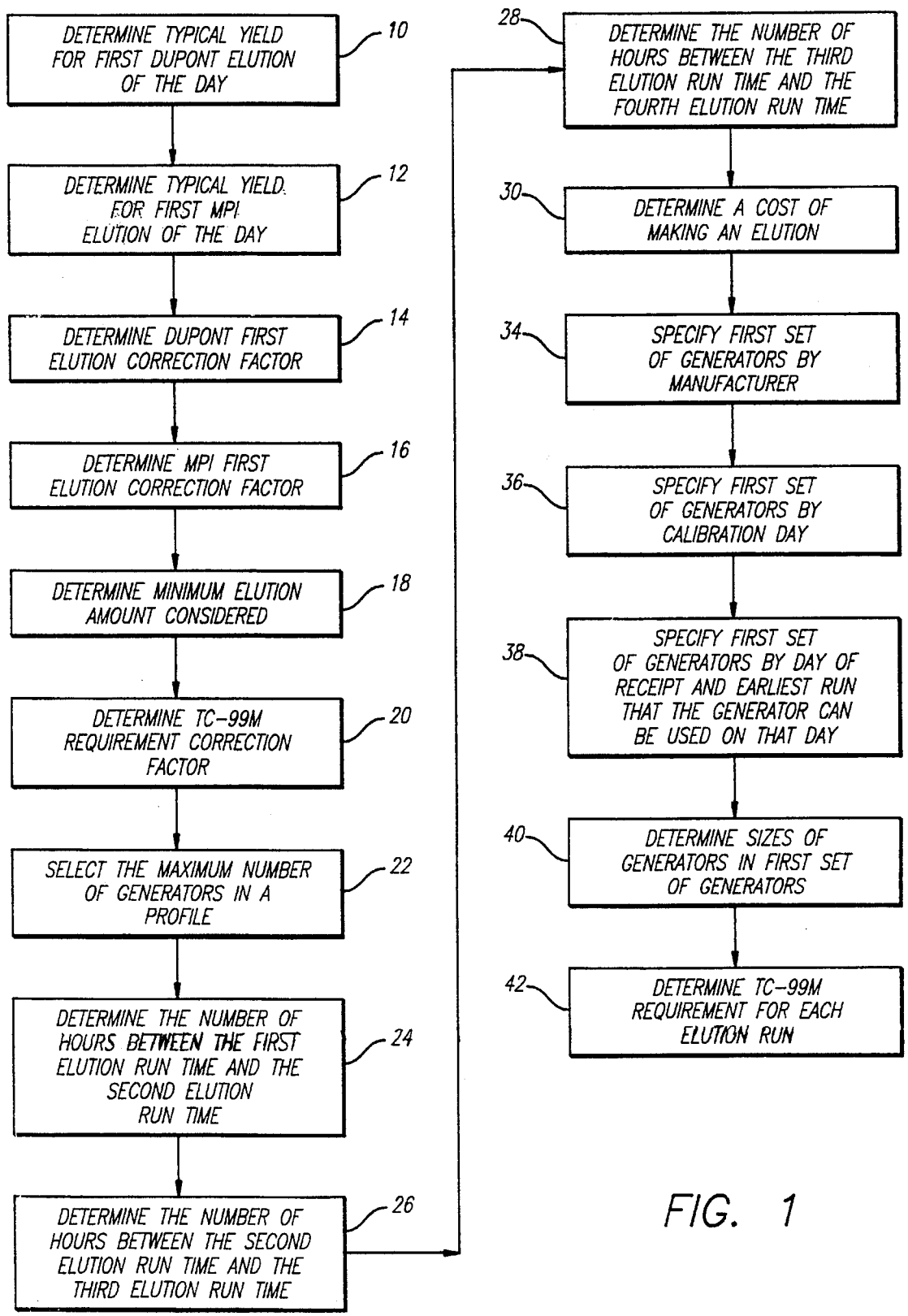
FIG. 1 is a simplified flowchart of the steps performed in the preferred method of the invention to determine the location information used to provide a preferred generator profile.

With reference to the drawings, and particularly to FIG. 1 thereof, a presently preferred method is illustrated to determine location information required to accurately provide a preferred generator profile for elution of a radioisotope. As used herein, a preferred generator profile, also called a preferred profile, is a set of generators capable of generating sufficient Tc-99m to meet an amount of radioisotope required for a preselected period of time, called a "total Tc-99m requirement." The preferred generator profile should also be efficient in terms of Tc-99m production, as compared to other possible sets of generators, to substantially reduce, if not minimize, wastage of radioactivity. As the Tc-99m requirement can vary between elution runs and between days of the preselected period of time, the need for Tc-99m may not remain constant for each elution run. Accordingly, the preferred generator profile must be able to yield varying amounts of Tc-99m over the course of the elution runs.

As discussed above, variable factors in the eluting environment, including manufacturer, influence the elution efficiency of a generator. These factors must be determined before a preferred generator profile can be provided. While the factors are determined in a specific order illustrated in FIG. 1 and in the corresponding description, any order may be used to determine these factors.

Initially, a typical yield for the first elution of the day is determined. This yield may vary by generator manufacturer, and therefore, it should be determined separately for each manufacturer. In the preferred embodiment, two manufacturers of generators, DuPont and MediPhysics, or MPI, are utilized, although other manufacturers may be incorporated without departing from the invention. For ease of discussion, primary reference to MPI and, in particular, DuPont will be used in examples herein. The first step 10 in the preferred embodiment is to determine a typical yield for the first elution of the day for DuPont generators. This number is expressed as a fraction of Mo-99 activity at noon. If, for example, the Tuesday morning yield of a Tuesday calibrated 2700 mCi generator is 2390 mCi, the elution efficiency of this elution is 2390/2700=0.885. In general, a default value of 0.85 is used. Then, in step 12, a typical yield for a first MPI elution of the day is calculated. This results in a number similar to the DuPont calculation described above, however, for MPI generators.

Many pharmacies or other locations wherein the present invention is utilized, report increased or depressed yields on the first elution of a generator. Consequently, a first elution correction factor should be determined for each manufacturer. Accordingly, in the preferred embodiment, in step 14, a DuPont first elution correction factor is determined. The DuPont first elution correction factor can be applied to the first elution of all DuPont generators. In this manner, if, in general, first DuPont elutions are depressed by ten percent (10%), a DuPont first elution correction factor of 0.9 would be applied when determining a yield of the first elution of a DuPont generator. Similarly, in step 16, a MPI first elution factor is determined.

The smallest elution yield of a generator that the method of the present invention will consider in providing a preferred generator profile should also be determined. Called a minimum elution amount, it should be the smallest practical elution yield utilized in the laboratory. Accordingly, in the preferred embodiment, a minimum elution amount considered is determined in step 18. In general, a default value of 200 mCi is utilized. In a more detailed embodiment of the present invention, a minimum elution amount considered in each elution run can be determined.

A factor for use in adjusting estimates of Tc-99m requirements should also be determined. This is a number by which all TC-99m requirements are multiplied prior to providing a preferred generator profile. If a laboratory is able to predict actual determined needs, this number should be one. If the Tc-99m needs cannot be accurately determined, for example, because they are based upon estimates, then the Tc-99m need correction factor will be set to a number other than one to adjust the estimate. Therefore, in step 20, a Tc-99m requirement correction factor is determined.

The maximum number of generators considered by the present invention in providing a preferred generator profile should be determined to improve the efficiency of the method. If the maximum number of generators is set too high, too many possible generator profiles will be generated and the method of the present invention will take an excessive amount of time. If the number is set too low, the method may not be able to find a preferred generator profile that will meet a total Tc-99m requirement. Therefore, in step 22, a maximum number of generators in a profile is selected. In selecting the maximum number of generators, prior experience with generators can be useful in selecting an optimum number. In general, a smaller pharmacy will need fewer Mo-99 generators to meet its total Tc-99m requirement, while a larger pharmacy will need more generators to meet its requirement.

The amount of Tc-99m in a generator is dependent, in part, on the amount of time since the generator was last eluted. Therefore, the number of hours between solution runs is useful in determining the amount of Tc-99m in the generator. In step 24, the number of hours between the first solution run time and the second solution run time are determined. In the preferred embodiment, a default value of four hours is utilized. Similarly, in steps 26 and 28, the number of hours between the second solution run time and the third elution run time, and the number of hours between the third elution run time and the fourth solution run time, respectively, are determined. The determination of the number of hours between solution runs can also be made by determining the day and time of each elution run. From there, the numbers of hours between elution runs can be calculated.

The cost of making an elution can raise the total cost of one profile over another if the first profile requires more elutions to meet the pharmacy's total Tc-99m requirement. This determination associates a cost of making an elution to more accurately reflect the cost of a profile. In step 30, a cost of making an elution is determined. For example, if the generators in a given profile require five elutions to meet the Tc-99m requirement, while the generators in a second profile only require three elutions, the total cost of eluting the generators will be higher for the first profile and may affect the determination of which profile is more cost efficient.

Just as the maximum number of generators in a preferred generator profile can be limited, the parameters of the generators that may be included in a profile can also be selected. For example, a pharmacy may want to only purchase DuPont generators, and it may not be practical for the pharmacy to use generators over 2700 mCi. The method of the present invention allows the user to customize its profiles by selecting a first set of generators from which possible generator profiles will be determined. Therefore, in the example above, a user may select only DuPont generators having 2700 mCi or less to be included in the first set of generators. Through this selection, the user will eliminate the possibility that the preferred generator profile will contain generators of such size or from such manufacturer that it cannot utilize.

To this end, the types and sizes of generators in the first set of generators is specified in steps 34 through 40. In step 34, the manufacturer for each of the generators in the first set is specified. In the preferred embodiment, as noted above, either DuPont or MPI generators can be designated. In step 36, the generator types in the first set are classified by calibration day, the day on which a generator contains its labelled amount of activity. In step 38, the generators in the first set are identified by day of receipt and by the earliest run that the generator can be used on the day of receipt.

Thus, in steps 34 through 38, the parameters for the first set of generators are specified. For example, it can be specified that the first set of generators has four generators, each manufactured by DuPont, and that one of the generators is calibrated on Friday, for receipt on Friday and may be used on the first run on the day of receipt. Further, it can be specified that a second generator is calibrated on Tuesday, for receipt on Monday and may be used by the third run of Monday. It can also be specified that a third generator is calibrated on Monday, for receipt on Tuesday and available for use on the first run of Tuesday. Finally, it can be specified that a fourth generator is calibrated on Thursday, for receipt on Friday and available for the first run of that day.

The sizes of the generators in the first set are specified in step 40. The maximum number of different sizes of first set generators specified in step 40 may differ from the maximum number of generators in a profile or the number of different generators in first set generators. If, for example, the generator sizes in the first set of generators are defined as 900 mCi and 1350 mCi, and the four different generator types (different in terms of manufacturer, calibration day, day of receipt or run available for use) have been specified, the method of the present invention will consider eight different generators (2 sizes×4 types) in providing a preferred generator profile.

To determine the total Tc-99m requirement for a preselected period of time, e.g., for a week, the total Tc-99m requirement must be broken down into Tc-99m requirements for each of the elution runs that will be performed over the week. Because the half-life of Tc-99m is short, it would be impractical for a pharmacy to obtain a single delivery of Tc-99m to meet its weekly requirement. Accordingly, Mo-99 generators are eluted periodically to extract Tc-99m when it is most needed and in a manner attempting to minimize wastage of radioactivity. To this end, a determination is made, in step 42, of the Tc-99m requirement for each elution run. The Tc-99m requirement is expressed in terms of mCi and should be determined for each day of the preselected period of time and for each run.

Figure 2:
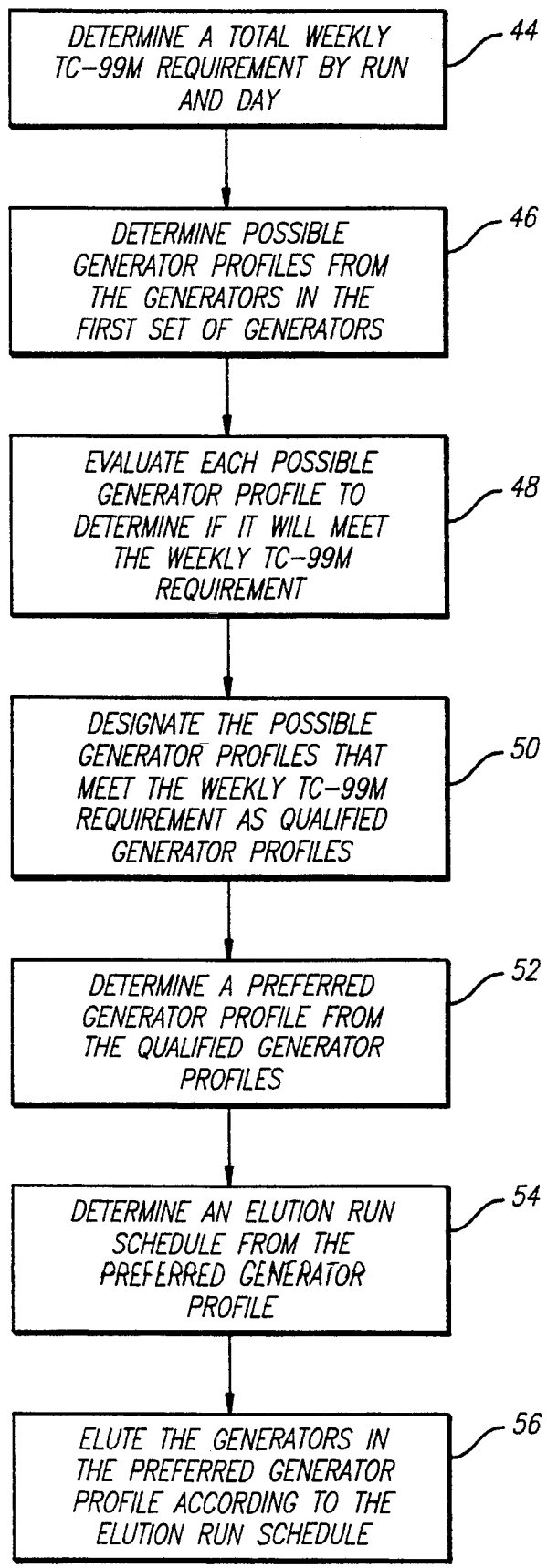
FIG. 2 is a simplified flowchart of the steps performed to provide a preferred generator profile and an elution run schedule.

Referring to FIG. 2, a method for providing a preferred generator profile and from there an elution run schedule based upon the location information determined above is shown. First, a summary of the elution runs Tc-99m requirements determined in step 42 is helpful in evaluating the profile of Mo-99 generators that will meet the Tc-99m requirements of the individual elution runs. Therefore, in step 44, a total Tc-99m requirement is determined by elution run and by day from the determinations made in step 42 above.

Prior to determining the preferred generator profile that will meet the total Tc-99m requirement, a determination of possible generator profiles is made, in step 46, from the types and sizes of first set generators determined in steps 32 through 40. Each possible generator profile is a different second set of generators that may be created from the first set generators, where the size of each second set is not greater than the maximum number of generators in a profile. Accordingly, if the maximum number of generators in a profile is three, the maximum number of generators in a second set is three. If the size of the first set of generators is eight, then there will be one hundred and sixty-five (165) different possible generator profiles.

However, if the maximum number of generators in a profile is three, and the size of the first set of generators is three, then there will be twenty different possible generator profiles. The twenty different possible generator profiles are illustrated below. Each alphabetical character represents a different first set generator, so that "A" represents one generator, "B" represents a second generator, and "C" represents a third generator. In the example, two characters represent a possible generator profile having two generators as specified by the letters. A zero is a profile without any generators. Therefore, the list of possible generator profiles from the example including a specification of three as the maximum number of generators in a profile and the specification of three first set generators is:

| 0 | AA | BC  | AAC | BBB |
|---|----|-----|-----|-----|
| A | AB | CC  | ABB | BBC |
| B | AC | AAA | ABC | BCC |
| C | BB | AAB | ACC | CCC |

Accordingly, one possible generator profile has two "A" generators and one "B" generator.

Next, in step 48, each possible generator profile is evaluated to determine if it will meet the total Tc-99m requirement. In the preferred embodiment, this evaluation is almost identical to a determination of an elution run schedule, which is described below. However, other methods of evaluating each possible generator profile can be utilized. If a possible generator profile meets the total Tc-99m requirement, it is designated in step 50 as a qualified generator profile. Once the selection of possible generator profiles has been narrowed down to those that meet the total Tc-99m requirement, the qualified generator profiles are evaluated in step 52 to provide a preferred generator profile that will minimize wastage of Tc-99m. Other considerations, such as the total cost of the generators in each qualified generator profile and the cost of making an elution may also be incorporated into the determination of the preferred generator profile.

In step 54, an elution run schedule is determined from the preferred generator profile. The method for determining the elution run schedule is shown in more detail in FIG. 3. The method may also be used to determine if a possible generator profile will meet a total Tc-99m requirement. The elution run schedule method determines which generator or set of generators from the preferred generator profile will be eluted to meet a "current" elution run Tc-99m requirement. Since every elution run is assigned as the "current" elution run, the method determines a group of generators for every elution run specified that will be eluted to meet the elution run's Tc-99m requirements. The method loops through each day and each elution run of the preselected period of time so that progressively each day is assigned as the "current" day and each elution run of each day is assigned as the "current" elution run.

By successively evaluating the Tc-99m yields of the generators in a generator profile at the time of each elution run, based upon the factors influencing the yield of each generator, accurate determinations can be made of a generator or set of generators that meets the current elution run Tc-99m requirement. In the preferred embodiment, the method of the present invention determines a third set of generators (a subset) from the profile generators that will meet the elution run Tc-99m requirement, with the least amount of available Tc-99m.

Elution of the generators in the preferred generator profile, according to the elution schedule determined in step 54, is performed in step 56. The preferred generator profile provides a road map by which a pharmacy may acquire generators for the preselected period of time. The preferred generator profile will contain the generators' parameters, e.g., manufacturer, calibration, size, day of receipt and earliest elution run that the generator can be used on the day of receipt. The elution schedule provides a road map for eluting the acquired generators. By following the elution schedule, the generators acquired by a pharmacy will provide sufficient Tc-99m at the time of each elution run to meet its Tc-99m requirement.

Figure 3:
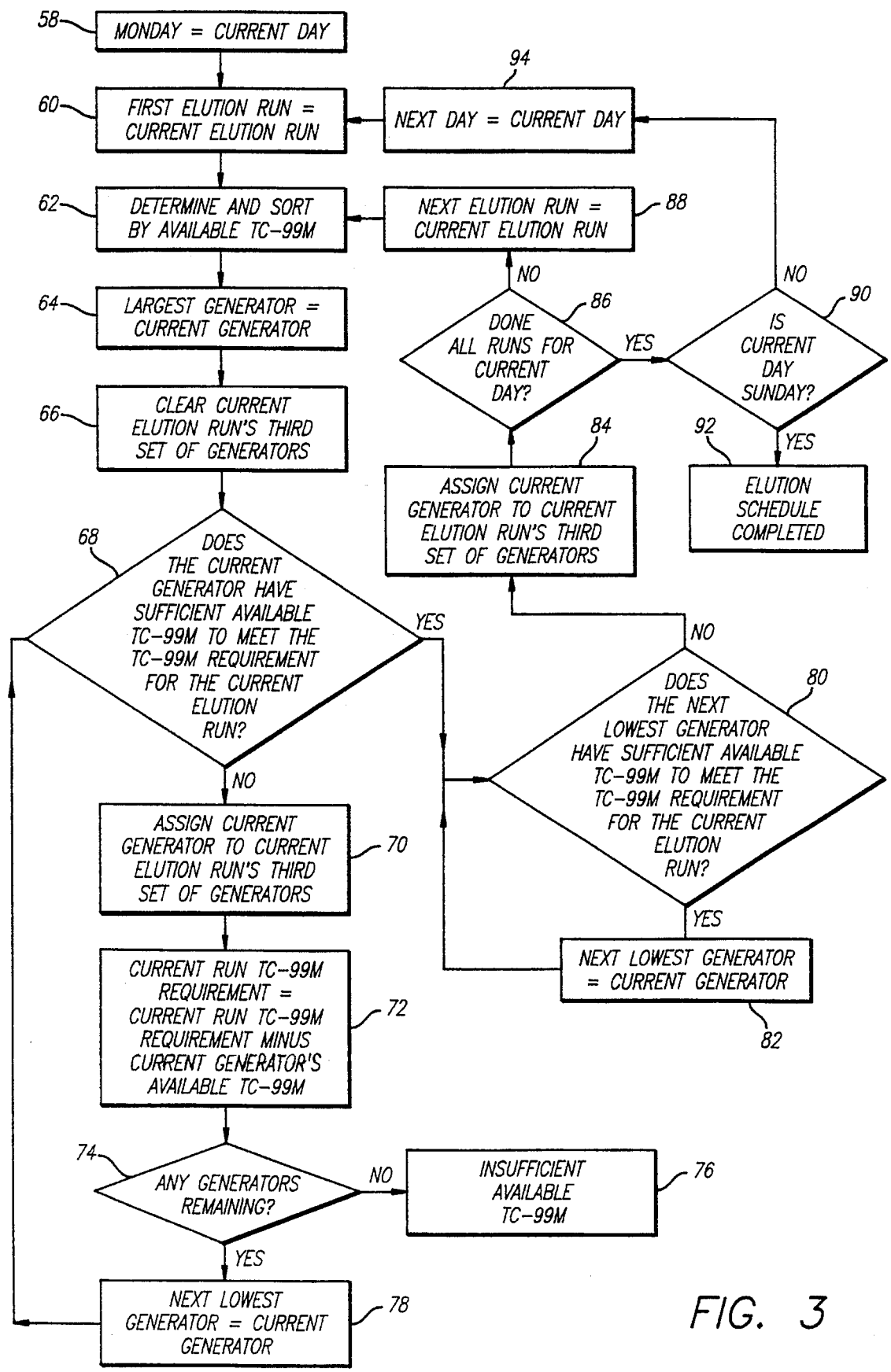
FIG. 3 is a detailed flowchart of the steps performed to determine an elution run schedule.

Referring to FIG. 3, the determination of an elution run schedule starts with the first day of the preselected period of time. As an example, Monday can be selected as the current day, in step 58, and in step 60, the first elution run of the current day is set as the current elution run. Following that, the available Tc-99m at the time of the current elution run is determined for each generator. The available Tc-99m may be influenced by the typical yield for the first elution of the day determined in steps 10 and 12 above. Further, if a generator is eluted for the first time, the first elution correction factor may affect the yield of a generator. The amount of time since the generator was last eluted and the amount Mo-99 in the generator will also affect its yield. Consequently, all of these factors must be considered to determine the amount of available Tc-99m in a generator at the time of a given elution run.

Subsequently, in step 62, the generators in the profile are sorted by available Tc-99m and, in step 64, the largest generator is assigned as the current generator. The largest generator is the generator with the largest amount of available Tc-99m. At this time, the third set of generators for the current elution run is cleared in step 66, so that no generators are pre-assigned for elution in the current elution run.

Once the levels of Tc-99m in each generator have been ascertained and the generators have been sorted by yield, the preferred method examines the profile generators to determine a third set of generators (a subset of the profile generators) that has a total amount of available Tc-99m that is not less than the Tc-99m requirement of the current elution run. The preferred method also examines the profile generators with a goal of using the generator or set of generators with the lowest Tc-99m available that will meet the Tc-99m requirement of the current elution run. Accordingly, in the preferred embodiment, the generator or set of generators that meet both criteria are assigned to the current elution run third set of generators, that is, the generators that are designated for elution in the current elution run. Later, the generators in the current elution run third set will be eluted to meet its Tc-99m requirement.

Accordingly, the method of the present invention evaluates in step 68 whether the current generator has sufficient available Tc-99m to meet the Tc-99m requirement for the current elution run. If the current generator does not have enough available Tc-99m to meet this requirement, then, in step 70 the current generator is assigned to the third set of generators for the current elution run, because at this point, the current generator has the highest available Tc-99m and no other generator will be able to meet the requirement either. From there, to determine the new Tc-99m requirement for the current elution run, the current generator's available Tc-99m is subtracted from the current run Tc-99m requirement in step 72.

Once the new Tc-99m requirement for the current elution run is determined, the profile is examined in step 74 to determine whether there are any uneluted generators remaining. Although a generator may contain some Tc-99m at the time of the elution run, the available Tc-99m may not meet the minimum elution amount considered, as determined in step 18. Accordingly, if the current generator cannot meet the current elution run requirement (step 68) and there are no other available generators (step 74), then, in step 76, it is determined that there is insufficient available Tc-99m and the profile cannot be used to meet the total Tc-99m requirement. If a possible generator profile is being evaluated to determine whether it can meet the total Tc-99m requirement, and the elution run schedule reaches step 76, then the possible generator profile should not be designated as a qualified generator profile.

Returning to step 74, if, on the other hand, there are other generators remaining in the profile, the next lowest generator, i.e., the generator with the next lowest amount of available Tc-99m, is assigned as the current generator in step 78. Following this assignment, the preferred method returns to step 68 where it is determined whether the new current generator has sufficient available Tc-99m to meet the new Tc-99m requirement of the current run.

Returning to step 68, the determination whether the current generator has sufficient available Tc-99m to meet the current elution run Tc-99m requirement is made again with the goal of using the lowest generator that will meet the Tc-99m requirement. Therefore, if the current generator can meet the requirement, then in step 80, the next lowest generator is evaluated to determine if it has sufficient available Tc-99m to meet this same requirement. Further, if the next lowest generator meets the current elution run Tc-99m requirement, then it becomes the current generator in step 82. From there, step 80 is repeated and the next lowest generator is evaluated to determine of it meets the current elution run Tc-99m requirement. This loop continues between steps 80 and 82 until either no generators are remaining in the profile, or the next lowest generator does not have sufficient 1available Tc-99m to meet the current elution run Tc-99m requirement. At that point, the current generator is the lowest generator that will meet the current elution run Tc-99m requirement and, in step 84, it is assigned to the third set of generators for the current elution run.

Once the method of the present invention has reached step 84, the Tc-99m requirement of the current elution run may be met by eluting the generators in its third set of generators. Accordingly, in step 86, it is then determined whether the current elution run is the last elution run for the current day. If it is not, the next elution run for the day becomes the current elution run, in step 88. From there, the method of the present invention returns to step 62 to begin the process of determining the lowest generator that will meet the new current elution run Tc-99m requirement, starting with determining the Tc-99m yields of the generators at the time of the new current elution run.

If, in step 86, it is determined that all the elution runs for the current day have been evaluated, then, in step 90, it is determined whether the current day is the last day in the preselected period of time. For example, if the last day is Sunday, when the current day is Sunday, all of the days in the week and all of the elution runs in those days have been evaluated, and, in step 92, the elution schedule is completed. If, however, the current day is not Sunday, then in step 94, the next day of the week is assigned as the current day and the method of the present invention returns to step 60 where the first elution run of the new current day is set as the current elution run. Although Monday and Sunday have been used for examples of starting and ending days, if a period of time other than a week is preselected for evaluation, appropriate starting and ending days should be used.

By evaluating the preferred generator profile in the manner described in steps 58 through 94, a schedule of which generators in the preferred generator profile should be eluted for each elution run (each elution run's third set of generators) is determined. However, as is observable from the result obtained in step 76, when it is determined that there is insufficient Tc-99m to meet the current elution run requirement, the method described in FIG. 3, may also be used to determine if a possible generator profile will meet the total Tc-99m requirement. If, at any given time it is determined that there are no generators remaining to meet the current run Tc-99m requirement, then a possible generator profile will not meet the total Tc-99m requirement and it should not be designated as a qualified generator profile.

It will be appreciated from the foregoing description that the present invention provides an improved method of providing a preferred generator profile that will meet a total Tc-99m requirement and of determining an elution run schedule. The present invention removes the guesswork inherent in the prior methods, yet allows the user to customize the method to meet the individual requirements of each user location.

Although the present invention has been described in detail with reference only to the presently preferred method, those of ordinary skill will appreciate that various modifications can be made without departing from the invention. For example, additional methods may be used for determining each elution run's third set of generators, that is the generators that are eluted to meet the current elution run Tc-99m requirement. One method is to start the analysis with the lowest generator and work through the generators to the first generator that meets the current elution run Tc-99m requirement. Another method is to determine all the possible subsets of generators in the preferred generator profile, determine the total available Tc-99m of each subset at the time of the elution run, and select the subset that meets the elution run Tc-99m requirement with the least wastage of radioactivity. Further, additional parameters, such as specifying a maximum number of elutions for each run, can be utilized to provide additional flexibility to the present invention. Accordingly, the invention is limited only by the following claims.

I claim:

1. A method for elution of a radioisotope according to an elution run schedule, comprising:

selecting a first set of generators;

determining qualified generator profiles, wherein each qualified generator profile includes a second set of generators, selected from the first set of generators, such that the generators in each qualified generator profile are capable of producing, by time and amount, an output of radioisotope not less than an amount of radioisotope required for a preselected period of time;

determining a preferred generator profile from the list of qualified generator profiles;

determining an elution run schedule that designates the group of generators from the preferred generator profile to elute during each elution run performed during the preselected period of time; and eluting one or more of the group of generators in the preferred generator profile designated by the elution run schedule.

2. The method of claim 1, wherein selecting a first set of generators, comprises:

determining generator size criterion;

determining generator calibration criterion; and assigning generators that meet the size criterion and the calibration criterion as the first set of generators.

3. The method of claim 2 wherein selecting a first set of generators, further comprises:

determining generator manufacturer criterion;

determining generator day of receipt criterion; and assigning generators that meet the size criterion, the calibration criterion, the manufacturer criterion and the day of receipt criterion as the first set of generators.

4. The method of claim 1, wherein determining qualified generator profiles, comprises:

determining a maximum number of generators in a qualified generator profile;

determining possible generator profiles, each possible generator profile including a second set of generators selected from the first set of generators, such that the number of generators in each possible generator profile is not greater than the maximum number of generators in a profile; and determining a possible generator profile is a qualified generator profile if the generators in the possible generator profile are capable of producing an output of radioisotope not less than the amount of radioisotope required for the preselected period of time.

5. The method of claim 4, wherein determining a possible generator profile is a qualified generator profile, comprises:

determining elution run times for the elution runs that will be performed during the preselected period of time;

for each solution run and using the generators in the second set of generators in the possible generator profile, determining generators for use in each elution run by determining a radioisotope requirement of the elution run;

determining the level of available radioisotope in each generator; and determining if there is a third set of generators with a total amount of available radioisotope that is not less than the radioisotope requirement of the elution run.

6. The method of claim 1, further comprising: determining an elution run schedule for elution runs from the preferred generator profile.

7. The method of claim 6, wherein determining an elution run schedule, comprises:

determining elution run times for the elution runs that will be performed during the preselected period of time;

for each elution run and using the generators in the set of generators in the preferred generator profile, determining generators for use in each elution run by determining a radioisotope requirement of the elution run;

determining the level of available radioisotope in each generator;

determining a third set of generators with a total amount of available radioisotope that is not less than the radioisotope requirement of the elution run; and assigning the third set of generators as the generators for use in the elution run.

8. The method of claim 7, wherein determining a third set of generators, comprises:

determining a third set of generators with a total amount of available radioisotope that is not less than the radioisotope requirement of the elution run, and with the least amount of available radioisotope remaining in the third set of generators after the radioisotope requirement of the elution run has been subtracted from total amount of radioisotope available in the third set.

9. A method for elution of a radioisotope according to an elution run schedule, comprising:

selecting a first set of generators, including
determining generator size criterion;
determining generator calibration criterion;
determining generator manufacturer criterion;
determining generator day of receipt criterion; and
assigning generators that meet the size criterion, the calibration criterion, the manufacturer criterion and the day of receipt criterion as the first set of generators;

determining a maximum number of generators in a qualified generator profile;

determining a set of possible generator profiles, each possible generator profile including generators selected from the first set of generators, such that the number of generators in each possible generator profile is not greater than the maximum number of generators in a profile;

determining a list of qualified generator profiles from the set of possible generator profiles, including for each possible generator profile, determining whether the generators in the possible generator profile are capable of producing, by time and amount, an output of radioisotope not less than the amount of radioisotope required for the preselected period of time;

determining a preferred generator profile from the list of qualified generator profiles;

determining an elution run schedule that designates the subset of generators from the preferred generator profile to elute during each elution run performed during the preselected period of time; and eluting the group of generators in the preferred generator profile designated by the elution run schedule.

10. The method of claim 9, wherein determining a list of qualified generator profiles from the set of possible generator profiles, comprises:

determining elution run times for the elution runs that will be performed during the preselected period of time;

for each possible generator profile and for each elution run time, determining generators for elution in each elution run by determining a radioisotope requirement of the elution run;

determining the level of available radioisotope in each generator in the possible generator profile; and determining if there is a third set of generators with a total amount of available radioisotope that is not less than the radioisotope requirement of the elution run.

11. The method of claim 10, wherein determining an elution run schedule, comprises:

determining elution run times for the elution runs that will be performed during the preselected period of time;

for each elution run, determining generators for use in the elution run by determining a radioisotope requirement of the elution run;

determining the level of available radioisotope in each generator in the preferred generator profile;

determining a subset of generators in the preferred generator profile with a total amount of available radioisotope that is not less than the radioisotope requirement of the elution run, and with the least amount of available radioisotope remaining in the subset of generators after the radioisotope requirement of the elution run has been subtracted from total amount of radioisotope available in the subset; and assigning the determined subset set of generators as the generators designated for use in the elution run.

12. A method for elution of a radioisotope according to an elution run schedule, comprising:

selecting a first set of generators, including
determining generator size criterion;
determining generator calibration criterion;
determining generator manufacturer criterion;
determining generator day of receipt criterion; and
assigning generators that meet the size criterion, the calibration criterion, the manufacturer criterion and the day of receipt criterion as the first set of generators;

determining qualified generator profiles, wherein each qualified generator profile includes a second set of generators, selected from the first set of generators, such that the generators in each qualified generator profile are capable of producing, by time and amount, an output of radioisotope not less than an amount of radioisotope required for a preselected period of time;

determining a preferred generator profile from the list of qualified generator profiles;

determining an elution run schedule that designates the subset of generators from the preferred generator profile to elute during each elution run performed during the preselected period of time, including determining elution run times for the elution runs that will be performed during the preselected period of time;

for each elution run, determining generators for use in the elution run by determining a radioisotope requirement of the elution run;

determining the level of available radioisotope in each generator in the preferred generator profile;

determining a subset of generators in the preferred generator profile with a total amount of available radioisotope that is not less than the radioisotope requirement of the elution run, and with the least amount of available radioisotope remaining in the subset of generators after the radioisotope requirement of the elution run has been subtracted from total amount of radioisotope available in the subset; and assigning the determined subset set of generators as the generators designated for use in the elution run; and eluting the group of generators in the preferred generator profile designated by the elution run schedule for use in the elution run.

* * * * *